(12) United States Patent
Li et al.

(10) Patent No.: US 9,464,109 B2
(45) Date of Patent: *Oct. 11, 2016

(54) METHOD FOR THE SELECTIVE ENRICHMENT AND LABELING OF PHOSPHORPROTEINS

(71) Applicant: Intel Corporation, Santa Clara, CA (US)

(72) Inventors: Handong Li, Santa Clara, CA (US); Narayan Sundararajan, Palo Alto, CA (US)

(73) Assignee: INTEL CORPORATION, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/501,764

(22) Filed: Sep. 30, 2014

(65) Prior Publication Data

US 2015/0031853 A1    Jan. 29, 2015

Related U.S. Application Data

(63) Continuation of application No. 11/529,541, filed on Sep. 29, 2006, now Pat. No. 8,859,734.

(51) Int. Cl.
*C07K 1/13* (2006.01)
*C07K 7/08* (2006.01)

(52) U.S. Cl.
CPC .. *C07K 1/13* (2013.01); *C07K 7/08* (2013.01)

(58) Field of Classification Search
CPC ................................... C07K 1/13; C07K 7/08
USPC ........................................................ 530/326
See application file for complete search history.

(56) References Cited

U.S. PATENT DOCUMENTS

| 6,426,190 | B1 | 7/2002 | Minden et al. |
| 7,163,803 | B2 | 1/2007 | Hamon et al. |
| 2003/0044848 | A1 | 3/2003 | Rush et al. |
| 2005/0176093 | A1* | 8/2005 | Ahn ................. G01N 33/6803 435/68.1 |
| 2006/0263886 | A1* | 11/2006 | Peters .................... C07B 59/00 436/56 |

OTHER PUBLICATIONS

NPL document titled RAMAN spectroscopy from http://www.chemsoc.org/ExamplarChem/entries/2004/birmingham_jones/raman.html (pp. 1-5).
NPL-definition of enrich from dictionary.com. Accessed May 28, 2008.
Pan S. Li H. Hong F, Yu B, Zhao K, Glycosyl donors with phosphorimidate leaving groups for either alpha or beta glycosidation, Tetrahedron Letters, 1997, 38 (35): 6139-6142.
NPL-STIC printout pp. 84-85 for the reaction scheme outlined in Parang et al above in (W). 2002.
Tao WA, Wollscheid B, O'Brien R, Eng JK, Li X, Bodenmiller B, Watts JD, Hood L, Aebersold R, Quantitative phosphoproteome analysis using a dendrimer conjugation chemistry and tandem mass spectrometry, Nature Methods, Aug. 2005, 2(8): 591-598.

* cited by examiner

*Primary Examiner* — Julie Ha
(74) *Attorney, Agent, or Firm* — Pillsbury Winthrop Shaw Pittman LLP

(57) ABSTRACT

A method for the introduction of a labeling structure such as fluorescent molecules or a Raman tag to a compound is described. Imidazole functionalized resins or polymers are used to selectively immobilize phosphocompounds without protecting the carboxylic groups is described. Relying on the pKa difference between amines and hydrazides and carrying out the reaction in a slightly acidic buffer, all of the amines are protected by protonation while the hydrazides react with the phosphate imidazolide to form a phosphoramidate bond.

11 Claims, 4 Drawing Sheets

SEQUENCE LISTING

```
<160> NUMBER OF SEQ ID NOS: 1

<210> SEQ ID NO 1
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: MOD_RES
<222> LOCATION: (3)..(3)
```

```
<223> OTHER INFORMATION: PHOSPHORYLATION

<400> SEQUENCE: 1

Phe Gln Ser Glu Glu Gln Gln Thr Glu Asp Glu Leu Gln Asp Lys
1               5                   10                  15
```

METHOD FOR THE SELECTIVE ENRICHMENT AND LABELING OF PHOSPHORPROTEINS

CROSS-REFERENCE RELATED APPLICATION

The current application is a continuation of U.S. patent application Ser. No. 11/529,541, filed Sep. 29, 2006, which will issue as U.S. Pat. No. 8,859,734 on Oct. 14, 2014. The disclosure of the prior application is considered part of and is incorporated by reference in the disclosure of this application.

FIELD OF INVENTION

In the illustrative embodiments, the invention relates to the use of the hydrolytic stability difference between, for example, phosphate imidazolide and carboxylate imidazolide. Imidazole functionalized resins or polymers are used to selectively immobilize phosphocompounds without protecting the carboxylic groups. Relying on the pKa difference between amines and hydrazides and carrying out the reaction in a slightly acidic buffer, all of the amines are protected by protonation while the hydrazides react with the phosphate imidazolide to form a phosphoramidate bond. This permits the introduction of a labeling structure such as a fluorescent molecules or a Raman tag.

BACKGROUND

Proteins are the most abundant macromolecules in cells, making up over half their dry weight. Proteins and peptides are known to carry chemical information in their tertiary structures. A number of proteins occurring in nature are conjugated to other chemical groups. Examples are lipoproteins, glycoproteins, phosphorproteins, hemoproteins, flavoproteins, and metalloproteins.

Proteins have diverse biological functions. Non-limiting examples are transport proteins (e.g., hemoglobin and serum albumin), nutrient and storage proteins (for example, gliadin, ovalbumin, casein, and ferritin); contractile or motile proteins (e.g., actin, myosin, tubulin, and dynein); structural proteins (for example, keratin, fibroin, collagen, elastin, and proteoglycans); defense proteins (e.g., antibodies, immunoglobulins, fibrinogen, thrombin, botulinus toxin, diphtheria toxin, snake venom, and ricin); enzymes, and regulatory proteins (e.g., insulin, growth hormone, corticotropin and repressors). Molecular imprinting techniques can be used to prepare a wide variety of mimics of these important compounds.

Among common constituents, the phosphate group is involved in many biomolecules, including proteins, lipids, carbohydrates and nucleic acids. Selective enrichment and derivatization of phosphate groups are important tools to analyze these biomolecules. For example, phosphoproteins are often present in compounds at low levels, thus a selective enrichment and labeling technique is essential to achieve detection.

Currently, enrichment and labeling of phosphorproteins is done in separate steps. Immobilized metal affinity chromatography and phosphor specific antibody resin are two standard tools for enriching phosphorproteins. Beta-elimination followed by Michael addition is commonly used to derivatize phosphate groups for improved detection sensitivity in mass spectrometry.

DETAILED DESCRIPTION

Figure 1:
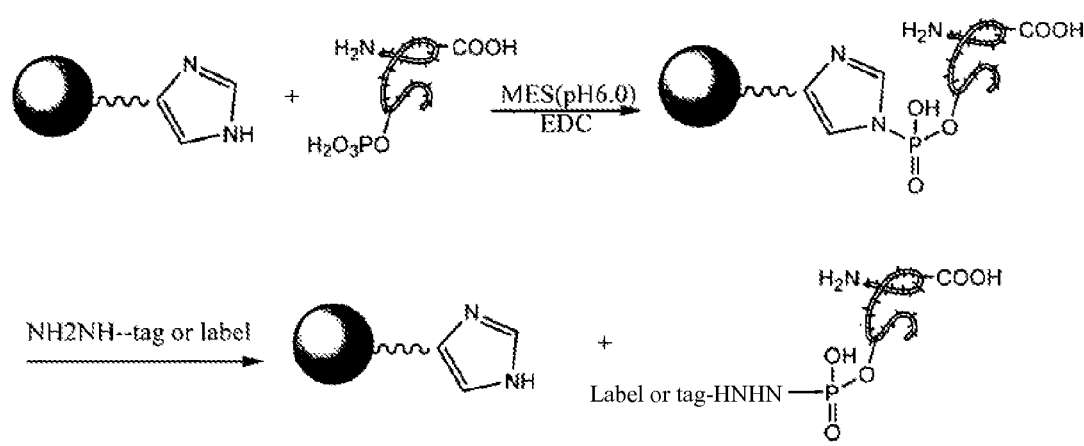
FIG. 1 is a representative illustration of an embodiment of the process of the present invention.

As used in the specification and claims, the singular forms "a", "an" and "the" include plural references unless the context clearly dictates otherwise.

As used herein, the term "pKa" refers to the negative log of the acid ionization constant of a compound. Generally, this may be thought of as the ability of an ionizable group of an organic compound to donate a proton ($H^+$) in an aqueous media. The computed quantity is a measure of its apparent pKa, or macroscopic dissociation constant, at equilibrium, normally taken at 25° C. In chemistry and biochemistry, the acid dissociation constant, the acidity constant, or the acid-ionization constant (Ka) is a specific type of equilibrium constant that indicates the extent of dissociation of hydrogen ions from an acid. The equilibrium is that of a proton transfer from an acid, HA, to water, $H_2O$. The term for the concentration of water, $[H_2O]$, is omitted from the general equilibrium constant expression:

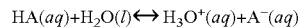

$$K_a = \frac{[H_3O^+][A^-]}{[HA]}$$

The equilibrium is often written in terms of "$H^+(aq)$", which reflects the Bronsted-Lowry Theory of acids.

Because this constant differs for each acid and varies over many degrees of magnitude, the acidity constant is often represented by the additive inverse of its common logarithm, represented by the symbol $pK_a$ (using the same mathematical relationship as $[H^+]$ is to pH).

$$pK_a = -\log_{10} K_a$$

In general, a larger value of $K_a$ (or a smaller value of $pK_a$) indicates a stronger acid, since the extent of dissociation is larger at the same concentration.

Using the acid dissociation constants, the concentration of acid, its conjugate base, protons and hydroxide can be easily determined. If an acid is partly neutralized, the Ka can also be used to find the pH of the resulting buffer. This same information is summarized in the Henderson-Hasselbalch equation.

A "nanomaterial" as used herein refers to a structure, a device or a system having a dimension at the atomic, molecular or macromolecular levels, in the length scale of approximately 1-100 nanometer range. Preferably, a nanomaterial has properties and functions because of the size and can be manipulated and controlled on the atomic level.

The term "target" or "target molecule" refers to a molecule of interest that is to be analyzed, e.g., a nucleotide, an oligonucleotide, or a protein. The target or target molecule could be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to molecular probes such as chemically modified carbon nanotubes, carbon nanotube bundles, nanowires, nanoclusters or nanoparticles. The target molecule may be fluorescently labeled DNA or RNA.

The term "probe" or "probe molecule" refers to a molecule that binds to a target molecule for the analysis of the target. The probe or probe molecule is generally, but not necessarily, has a known molecular structure or sequence. The probe or probe molecule is generally, but not necessarily, attached to the substrate of the array. The probe or probe molecule is typically a nucleotide, an oligonucleotide, or a protein, including, for example, cDNA or pre-synthesized polynucleotide deposited on the array. Probes molecules are biomolecules capable of undergoing binding or molecular recognition events with target molecules. (In some references, the terms "target" and "probe" are defined opposite to the definitions provided here.) The polynucleotide probes require the sequence information of genes, and thereby can exploit the genome sequences of an organism. In cDNA arrays, there could be cross-hybridization due to sequence homologies among members of a gene family. Polynucleotide arrays can be specifically designed to differentiate between highly homologous members of a gene family as well as spliced forms of the same gene (exon-specific). Polynucleotide arrays of the embodiment of this invention could also be designed to allow detection of mutations and single nucleotide polymorphism. A probe or probe molecule can be a capture molecule.

A "compound" refers to a macroscopically homogeneous substance consisting of atoms or ions of two or more different elements in definite proportions that cannot be separated by physical means. A compound's composition is constant. A compound usually, has properties unlike those of its constituent elements.

The term "intermediate compound" refers to a substance formed at an intermediate stage before the formation of a desired end product of a chemical reaction, synthesis or a substance. The intermediate compound is formed in the course of the chemical reaction or synthesis of the desired end product and participates in the chemical reaction or synthesis until it is either deactivated or consumed.

The term "derivatization compound" refers to a substance that can be made from a parent substance or a compound derived or obtained from another compound and contains essential elements of the parent substance or said another compound. The derivatization compound may be made from the parent substance or a chemical substance related structurally to the parent substance and theoretically derivable from the parent substance. The derivatization compound may also be produced from another compound of similar structure in one or more steps.

The term "molecule" generally refers to a macromolecule or polymer as described herein. However, arrays comprising single molecules, as opposed to macromolecules or polymers, are also within the scope of the embodiments of the invention.

A "macromolecule" or "polymer" comprises two or more monomers covalently joined. The monomers may be joined one at a time or in strings of multiple monomers, ordinarily known as "oligomers." Thus, for example, one monomer and a string of five monomers may be joined to form a macromolecule or polymer of six monomers. Similarly, a string of fifty monomers may be joined with a string of hundred monomers to form a macromolecule or polymer of one hundred and fifty monomers. The term polymer as used herein includes, for example, both linear and cyclic polymers of nucleic acids, polynucleotides, polynucleotides, polysaccharides, oligosaccharides, proteins, polypeptides, peptides, phospholipids and peptide nucleic acids (PNAs). The peptides include those peptides having either $\alpha$-, $\beta$-, or $\omega$-amino acids. In addition, polymers include heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which could be apparent upon review of this disclosure.

The term "nucleotide" includes deoxynucleotides and analogs thereof. These analogs are those molecules having some structural features in common with a naturally occurring nucleotide such that when incorporated into a polynucleotide sequence, they allow hybridization with a complementary polynucleotide in solution. Typically, these analogs are derived from naturally occurring nucleotides by replacing and/or modifying the base, the ribose or the phosphodiester moiety. The changes can be tailor-made to stabilize or destabilize hybrid formation, or to enhance the specificity of hybridization with a complementary polynucleotide sequence as desired, or to enhance stability of the polynucleotide.

The term "polynucleotide" or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribopolynucleotide (DNA), ribopolynucleotide (RNA), or DNA copies of ribopolynucleotide (cDNA) which may be isolated from natural sources, recombinantly produced, or artificially synthesized. A further example of a polynucleotide of the embodiments of the invention may be polyamide polynucleotide (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as "nucleotide polymers.

An "oligonucleotide" is a polynucleotide having 2 to 20 nucleotides. Analogs also include protected and/or modified monomers as are conventionally used in polynucleotide synthesis. As one of skill in the art is well aware, polynucleotide synthesis uses a variety of base-protected nucleoside derivatives in which one or more of the nitrogens of the purine and pyrimidine moiety are protected by groups such as dimethoxytrityl, benzyl, tert-butyl, isobutyl and the like.

When the macromolecule of interest is a peptide, the amino acids can be any amino acids, including a, $\beta$, or $\omega$-amino acids. When the amino acids are $\alpha$-amino acids, either the L-optical isomer or the D-optical isomer may be used. Additionally, unnatural amino acids, for example, $\beta$-alanine, phenylglycine and homoarginine are also contemplated by the embodiments of the invention. These amino acids are well-known in the art.

A "peptide" is a polymer in which the monomers are amino acids and which are joined together through amide bonds and alternatively referred to as a polypeptide. In the context of this specification it should be appreciated that the amino acids may be the L-optical isomer or the D-optical isomer. Peptides are two or more amino acid monomers long, and often more than 20 amino acid monomers long.

A "protein" is a long polymer of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, function, and regulation of the body's cells, tissues, and organs, and each protein has unique functions. Examples are hormones, enzymes, and antibodies.

The term "sequence" refers to the particular ordering of monomers within a macromolecule and it may be referred to herein as the sequence of the macromolecule.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." For example, hybridization refers to the formation of hybrids between a probe polynucleotide (e.g., a polynucleotide of the invention which may include substitutions, deletion, and/or additions) and a specific target polynucleotide (e.g., an analyte polynucleotide) wherein the probe preferentially hybridizes to the specific target polynucleotide and substantially does not hybridize to polynucleotides consisting of sequences which are not substantially complementary to the target polynucleotide. However, it could be recognized by those of skill that the minimum length of a polynucleotide desired for specific hybridization to a target polynucleotide could depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others.

Methods for conducting polynucleotide hybridization assays have been well developed in the art. Hybridization assay procedures and conditions could vary depending on the application and are selected in accordance with the general binding methods known in the art.

It is appreciated that the ability of two single stranded polynucleotides to hybridize could depend upon factors such as their degree of complementarity as well as the stringency of the hybridization reaction conditions.

As used herein, "stringency" refers to the conditions of a hybridization reaction that influence the degree to which polynucleotides hybridize. Stringent conditions can be selected that allow polynucleotide duplexes to be distinguished based on their degree of mismatch. High stringency is correlated with a lower probability for the formation of a duplex containing mismatched bases. Thus, the higher the stringency, the greater the probability that two single-stranded polynucleotides, capable of forming a mismatched duplex, could remain single-stranded. Conversely, at lower stringency, the probability of formation of a mismatched duplex is increased.

The appropriate stringency that could allow selection of a perfectly-matched duplex, compared to a duplex containing one or more mismatches (or that could allow selection of a particular mismatched duplex compared to a duplex with a higher degree of mismatch) is generally determined empirically. Means for adjusting the stringency of a hybridization reaction are well-known to those of skill in the art.

A "ligand" is a molecule that is recognized by a particular receptor. Examples of ligands that can be investigated by this invention include, but are not restricted to, agonists and antagonists for cell membrane receptors, toxins and venoms, viral epitopes, hormones, hormone receptors, peptides, enzymes, enzyme substrates, cofactors, drugs (e.g. opiates, steroids, etc.), lectins, sugars, polynucleotides, nucleic acids, oligosaccharides, proteins, and monoclonal antibodies.

A "receptor" is molecule that has an affinity for a given ligand. Receptors may-be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term "receptors" is used herein, no difference in meaning is intended. A "ligand receptor pair" is formed when two macromolecules have combined through molecular recognition to form a complex. Other examples of receptors which can be investigated by this invention include but are not restricted to:

a) Microorganism receptors: Determination of ligands which bind to receptors, such as specific transport proteins or enzymes essential to survival of microorganisms, is useful in developing a new class of antibiotics. Of particular value could be antibiotics against opportunistic fungi, protozoa, and those bacteria resistant to the antibiotics in current use.

b) Enzymes: For instance, one type of receptor is the binding site of enzymes such as the enzymes responsible for cleaving neurotransmitters; determination of ligands which bind to certain receptors to modulate the action of the enzymes which cleave the different neurotransmitters is useful in the development of drugs which can be used in the treatment of disorders of neurotransmission.

c) Antibodies: For instance, the invention may be useful in investigating the ligand-binding site on the antibody molecule which combines with the epitope of an antigen of interest; determining a sequence that mimics an antigenic epitope may lead to the-development of vaccines of which the immunogen is based on one or more of such sequences or lead to the development of related diagnostic agents or compounds useful in therapeutic treatments such as for auto-immune diseases (e.g., by blocking the binding of the "anti-self" antibodies).

d) Nucleic Acids: Sequences of nucleic acids may be synthesized to establish DNA or RNA binding sequences.

e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant.

f) Hormone receptors: Examples of hormones receptors include, e.g., the receptors for insulin and growth hormone. Determination of the ligands which bind with high affinity to a receptor is useful in the development of, for example, an oral replacement of the daily injections which diabetics take to relieve the symptoms of diabetes. Other examples are the vasoconstrictive hormone receptors; determination of those ligands which bind to a receptor may lead to the development of drugs to control blood pressure.

g) Opiate receptors: Determination of ligands which bind to the opiate receptors in the brain is useful in the development of less-addictive replacements for morphine and related drugs.

The term "specific binding" or "specific interaction" is the specific recognition of one of two different molecules for the other compared to substantially less recognition of other molecules. Generally, the molecules have areas on their surfaces or in cavities giving rise to specific recognition between the two molecules. Exemplary of specific binding are antibody-antigen interactions, enzyme—substrate interactions, polynucleotide hybridization interactions, and so forth.

The term "bi-functional linker group" refers to an organic chemical compound that has at least two chemical groups or moieties, such are, carboxyl group, amine group, thiol group, aldehyde group, epoxy group, that can be covalently modified specifically; the distance between these groups is equivalent to or greater than 5-carbon bonds.

The phrase "SERS active material," "SERS active particle," or "SERS cluster" refers to a material, a particle or a cluster of particles that produces a surface-enhanced Raman scattering effect. The SERS active material or particle generates surface enhanced Raman signal specific to the analyte molecules when the analyte-particle complexes are excited with a light source as compared to the Raman signal from the analyte alone in the absence of the SERS active material or SERS active particle. The enhanced Raman scattering effect provides a greatly enhanced Raman signal from Raman-active analyte molecules that have been adsorbed onto certain specially-prepared SERS active surfaces. The SERS active surface could be planar or curved. Typically, the SERS active surfaces are metal surfaces. Increases in the intensity of Raman signal could be in the order of $10^4$-$10^{14}$ for some systems. SERS active material or particle includes a variety of metals including coinage (Au, Ag, Cu), alkalis (Li, Na, K), Al, Pd and Pt. In the case of SERS active particle, the particle size of SERS active particles could range from 1 to 5000 nanometers, preferably in the range of 5 to 250 nanometers, more preferably in the range of 10 to 150 nanometers, and most preferably 40 to 80 nanometers.

The term "capture particle" refers to a particle that can capture an analyte. The capture particle could be a coinage metal nanoparticle with surface modification to allow strong physical and/or chemical adsorption of analyte molecules and to allow adhesion of "enhancer particles" by electrostatic attraction, through specific interaction using a linker such as antibody-antigen, DNA hybridization, etc. or through the analyte molecule.

The term "enhancer particle" refers to a SERS active particle with suitable surface modification, a linker or an analyte which combines with a capture particle to form an aggregate. In case the capture particle is positively charged, then a negatively charged SERS active particle can be used as an enhancer particle without a linker, and vise versa. In case the capture particle has an antigen or an antibody, then a SERS active particle having a complimentary linker, namely, an antibody or an antigen, could be used as an enhancer particle.

The term "tagged particle" refers a SERS active particle having one or more different Raman active labels attached to the SERS active particle by direct attachment or through a surface modification. A tagged particle has a linker that can link to another tagged particle via an analyte.

As used herein, the term "colloid" refers to nanometer size metal particles suspending in a liquid, usually an aqueous solution. In the methods of the invention, the colloidal particles are prepared by mixing metal cations and reducing agent in aqueous solution prior to heating. Typical metals contemplated for use in the practice of the invention include, for example, silver, gold, platinum, copper, and the like. A variety of reducing agents are contemplated for use in the practice of the invention, such as, for example, citrate, borohydride, ascorbic acid and the like. Sodium citrate is used in certain embodiments of the invention. Typically, the metal cations and reducing agent are each present in aqueous solution at a concentration of at least about 0.5 mM. After mixing the metal cations and reducing agent, the solution is heated for about 30 minutes. In some embodiments, the solution is heated for about 60 minutes. Typically, the solution is heated to about 95° C. In other embodiments, the solution is heated to about 100° C. Heating of the solution is accomplished in a variety of ways well known to those skilled in the art. In some embodiments, the heating is accomplished using a microwave oven, a convection oven, or a combination thereof. The methods for producing metallic colloids described herein are in contrast to prior methods wherein a boiling silver nitrate solution is titrated with a sodium citrate solution. This titration method can produce one batch of silver particles with adequate Raman enhancement to dAMP in about 10 attempts, and the other batches have low or no Raman activity at all. However, by employing the methods of the invention, an average SERS signal enhancement of 150% is observed relative to colloids prepared from the titration method.

The metallic colloids could be modified by attaching an organic molecule to the surface of the colloids. Organic molecules contemplated would typically be less than about 500 Dalton in molecular weight, and are bifunctional organic molecules. As used herein, a "bifunctional organic molecule" means that the organic molecule has a moiety that has an affinity for the metallic surface, and a moiety that has an affinity for a biomolecule. Such surface modified metallic colloids exhibit an increased ability to bind biomolecules, thereby resulting in an enhanced and reproducible SERS signal. The colloids can be used either individually, or as aggregates for binding certain biomolecules.

Organic molecules contemplated for use include molecules having any moiety that exhibits an affinity for the metals contemplated for use in the methods of the invention (i.e., silver, gold, platinum, copper, aluminum, and the like), and any moiety that exhibit affinities for biomolecules. For example, with regard to silver or gold affinity, in some embodiments, the organic molecule has a sulfur containing moiety, such as for example, thiol, disulfide, and the like. With regard to affinity for a biomolecule such as a polynucleotide, for example, the organic molecule has a carboxylic acid moiety. In certain embodiments, the organic molecule is thiomalic acid, L-cysteine diethyl ester, S-carboxymethyl-L-cysteine, cystamine, meso-2,3-dimercaptosuccinic acid, and the like. It is understood, however, that any organic molecule that meets the definition of a "bifunctional organic molecule", as described herein, is contemplated for use in the practice of the invention. It is also understood that the organic molecule may be attached to the metallic surface and the biomolecule either covalently, or non-covalently. Indeed, the term "affinity" is intended to encompass the entire spectrum of chemical bonding interactions.

This surface modification of metallic colloids provides certain advantages in SERS detection analyses. For example, the surfaces of the metallic colloids could be tailored to bind to a specific biomolecule or the surfaces can be tailored to differentiate among groups of proteins based on the side chains of the individual amino acid residues found in the protein.

The term "COIN" refers to a composite-organic-inorganic nanoparticle(s). The COIN could be surface-enhanced Raman scattering (SERS, also referred to as surface-enhanced Raman spectroscopy)-active nanoclusters incorporated into a gel matrix and used in certain other analyte separation techniques described herein.

COINs are composite organic-inorganic nanoclusters. The clusters include several fused or aggregated metal particles with a Raman-active organic compound adsorbed on the metal particles and/or in the junctions of the metal particles. Organic Raman labels can be incorporated into the coalescing metal particles to form stable clusters and produce intrinsically enhanced Raman scattering signals. The interaction between the organic Raman label molecules and the metal colloids has mutual benefits. Besides serving as signal sources, the organic molecules promote and stabilize metal particle association that is in favor of SERS. On the other hand, the metal particles provide spaces to hold and stabilize Raman label molecules, especially in the cluster junctions.

These SERS-active probe constructs comprise a core and a surface, wherein the core comprises a metallic colloid comprising a first metal and a Raman-active organic compound. The COINs can further comprise a second metal different from the first metal, wherein the second metal forms a layer overlying the surface of the nanoparticle. The COINs can further comprise an organic layer overlying the metal layer, which organic layer comprises the probe. Suitable probes for attachment to the surface of the SERS-active nanoclusters include, without limitation, antibodies, antigens, polynucleotides, oligonucleotides, receptors, ligands, and the like.

The metal required for achieving a suitable SERS signal is inherent in the COIN, and a wide variety of Raman-active organic compounds can be incorporated into the particle. Indeed, a large number of unique Raman signatures can be created by employing nanoclusters containing Raman-active organic compounds of different structures, mixtures, and ratios. Thus, the methods described herein employing COINs are useful for the simultaneous detection of many multiple components such as analytes in a sample, resulting in rapid qualitative analysis of the contents of "profile" of a body fluid. In addition, since many COINs can be incorporated into a single nanoparticle, the SERS signal from a single COIN particle is strong relative to SERS signals obtained from Raman-active materials that do not contain the nanoclusters described herein as COINs. This situation results in increased sensitivity compared to Raman-techniques that do not utilize COINs.

COINs could be prepared using standard metal colloid chemistry. The preparation of COINs also takes advantage of the ability of metals to adsorb organic compounds. Indeed, since Raman-active organic compounds are adsorbed onto the metal during formation of the metallic colloids, many Raman-active organic compounds can be incorporated into the COIN without requiring special attachment chemistry.

In general, the COINs could be prepared as follows. An aqueous solution is prepared containing suitable metal cations, a reducing agent, and at least one suitable Raman-active organic compound. The components of the solution are then subject to conditions that reduce the metallic cations to form neutral, colloidal metal particles. Since the formation of the metallic colloids occurs in the presence of a suitable Raman-active organic compound, the Raman-active organic compound is readily adsorbed onto the metal during colloid formation. COINs of different sizes can be enriched by centrifugation.

Typically, organic compounds are attached to a layer of a second metal in COINs by covalently attaching organic compounds to the surface of the metal layer Covalent attachment of an organic layer to the metallic layer can be achieved in a variety ways well known to those skilled in the art, such as, for example, through thiol-metal bonds. In alternative embodiments, the organic molecules attached to the metal layer can be crosslinked to form a molecular network.

The COIN(s) can include cores containing magnetic materials, such as, for example, iron oxides, and the like such that the COIN is a magnetic COIN. Magnetic COINs can be handled without centrifugation using commonly available magnetic particle handling systems. Indeed, magnetism can be used as a mechanism for separating biological targets attached to magnetic COIN particles tagged with particular biological probes.

The term "reporter" means a detectable moiety. The reporter can be detected, for example, by Raman spectroscopy. Generally, the reporter and any molecule linked to the reporter can be detected without a second binding reaction. The reporter can be COIN (composite-organic-inorganic nanoparticle), magnetic-COIN, quantum dots, and other Raman or fluorescent tags, for example.

As used herein, "Raman-active organic compound" refers to an organic molecule that produces a unique SERS signature in response to excitation by a laser. A variety of Raman-active organic compounds are contemplated for use as components in COINs. In certain embodiments, Raman-active organic compounds are polycyclic aromatic or heteroaromatic compounds. Typically the Raman-active organic compound has a molecular weight less than about 300 Daltons.

Additional, non-limiting examples of Raman-active organic compounds useful in COINs include TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluoresceins, aminoacridine, and the like.

In certain embodiments, the Raman-active compound is adenine, adenine, 4-amino-pyrazolo(3,4-d)pyrimidine, 2-fluoroadenine, N6-benzolyadenine, kinetin, dimethyl-allyl-amino-adenine, zeatin, bromo-adenine, 8-aza-adenine, 8-azaguanine, 6-mercaptopurine, 4-amino-6-mercaptopyrazolo(3,4-d)pyrimidine, 8-mercaptoadenine, or 9-amino-acridine 4-amino-pyrazolo(3,4-d)pyrimidine, or 2-fluoroadenine. In one embodiment, the Raman-active compound is adenine.

When "fluorescent compounds" are incorporated into COINs, the fluorescent compounds can include, but are not limited to, dyes, intrinsically fluorescent proteins, lanthanide phosphors, and the like. Dyes useful for incorporation into COINs include, for example, rhodamine and derivatives, such as Texas Red, ROX (6-carboxy-X-rhodamine), rhodamine-NHS, and TAMRA (5/6-carboxytetramethyl rhodamine NHS); fluorescein and derivatives, such as 5-bromomethyl fluorescein and FAM (5'-carboxyfluorescein NHS), Lucifer Yellow, IAEDANS, 7-Me$_2$, N-coumarin-4-acetate, 7-OH-4-CH$_3$-coumarin-3-acetate, 7-NH$_2$-4CH$_3$-coumarin-3-acetate (AMCA), monobromobimane, pyrene trisulfonates, such as Cascade Blue, and monobromotrimethyl-ammoniobimane.

Multiplex testing of a complex sample could generally be based on a coding system that possesses identifiers for a large number of reactants in the sample. The primary variable that determines the achievable numbers of identifiers in currently known coding systems is, however, the physical dimension. Tagging techniques, based on surface-enhanced Raman scattering (SERS) of fluorescent dyes, could be used in the embodiments of this invention for developing chemical structure-based coding systems.

Multiplex testing of a complex sample would generally be based on a coding system that possesses identifiers for a large number of reactants in the sample. The primary variable that determines the achievable numbers of identifiers in currently known coding systems is, however, the physical dimension. Techniques, based on surface-enhanced Raman scattering (SERS) of organic compounds, could be used in the embodiments of this invention for developing chemical structure-based coding systems. The organic compound-assisted metal fusion (OCAM) method could be used to produce composite organic-inorganic nanoparticles (COIN) that are highly effective in generating SERS signals allows synthesis of COIN labels from a wide range of organic compounds to produce sufficient distinguishable COIN Raman signatures to assay any complex biological sample. Thus COIN particles may be used as a coding system for multiplex and amplification-free detection of bioanalytes at near single molecule levels.

COIN particles generate intrinsic SERS signal without additional reagents. Using the OCAMF-based COIN synthesis chemistry, it is possible to generate a large number of different COIN signatures by mixing a limited number of Raman labels for use in multiplex assays in different ratios and combinations. In a simplified scenario, the Raman signature of a sample labeled with COIN particles may be characterized by three parameters: (a) peak position (designated as L), which depends on the chemical structure of Raman labels used and the number of available labels, (b) peak number (designated as M), which depends on the number of labels used together in a single COIN, and (c) peak height (designated as i), which depends on the ranges of relative peak intensity.

The total number of possible distinguishable Raman signatures (designated as T) may be calculated from the following equation:

$$T = \sum_{k=1}^{M} \frac{L!}{(L-k)!k!} P(i,k)$$

where P(i,k)=i$^k$-i+1, being the intensity multiplier which represents the number of distinct Raman spectra that may be generated by combining k (k=1 to M) labels for a given i value. The multiple organic compounds may be mixed in various combinations, numbers and ratios to make the multiple distinguishable Raman signatures. It has been shown that spectral signatures having closely positioned peaks (15 cm$^{-1}$) may be resolved visually. Theoretically, over a million of Raman signatures may be made within the Raman shift range of 500-2000 cm$^{-1}$ by incorporating multiple organic molecules into COIN as Raman labels using the OCAMF-based COIN synthesis chemistry.

Thus, OCAMF chemistry allows incorporation of a wide range of Raman labels into metal colloids to perform parallel synthesis of a large number of COIN labels with distinguishable Raman signatures in a matter of hours by mixing several organic Raman-active compounds of different structures, mixtures, and ratios for use in the invention methods described herein.

COINs may be used to detect the presence of a particular target analyte, for example, a nucleic acid, oligonucleotide, protein, enzyme, antibody or antigen. The nanoclusters may also be used to screen bioactive agents, i.e. drug candidates, for binding to a particular target or to detect agents like pollutants. Any analyte for which a probe moiety, such as a peptide, protein, oligonucleotide or aptamer, may be designed can be used in combination with the disclosed nanoclusters.

Also, SERS-active COINs that have an antibody as binding partner could be used to detect interaction of the Raman-active antibody labeled constructs with antigens either in solution or on a solid support. It could be understood that such immunoassays can be performed using known methods such as are used, for example, in ELISA assays, Western blotting, or protein arrays, utilizing a SERS-active COIN having an antibody as the probe and acting as either a primary or a secondary antibody, in place of a primary or secondary antibody labeled with an enzyme or a radioactive compound. In another example, a SERS-active COIN is attached to an enzyme probe for use in detecting interaction of the enzyme with a substrate.

Another group of exemplary methods could use the SERS-active COINs to detect a target nucleic acid. Such a method is useful, for example, for detection of infectious agents within a clinical sample, detection of an amplification product derived from genomic DNA or RNA or message RNA, or detection of a gene (cDNA) insert within a clone. For certain methods aimed at detection of a target polynucleotide, an oligonucleotide probe is synthesized using methods known in the art. The oligonucleotide is then used to functionalize a SERS-active COIN. Detection of the specific Raman label in the SERS-active COIN identifies the nucleotide sequence of the oligonucleotide probe, which in turn provides information regarding the nucleotide sequence of the target polynucleotide.

The term "complementary" refers to the topological compatibility or matching together of interacting surfaces of a ligand molecule and its receptor. Thus, the receptor and its ligand can be described as complementary, and furthermore, the contact surface characteristics are complementary to each other.

The terms "spectrum" or "spectra" refer to the intensities of electromagnetic radiation as a function of wavelength or other equivalent units, such as wavenumber, frequency, and energy level.

The term "spectrometer" refers to an instrument equipped with scales for measuring wavelengths or indexes of refraction.

The term "dispersive spectrometer" refers to a spectrometer that generates spectra by optically dispersing the incoming radiation into its frequency or spectral components. Dispersive spectrometers can be further classified into two types: monochromators and spectrographs. A monochromator uses a single detector, narrow slit(s) (usually two, one at the entrance and another at the exit port), and a rotating dispersive element allowing the user to observe a selected range of wavelength. A spectrograph, on the other hand, uses an array of detector elements and a stationary dispersive element. In this case, the slit shown in the figure is removed, and spectral elements over a wide range of wavelengths are obtained at the same time, therefore providing faster measurements with a more expensive detection system.

The term "analyte" means any atom, chemical, molecule, compound, composition or aggregate of interest for detection and/or identification. Examples of analytes include, but are not limited to, an amino acid, peptide, polypeptide, protein, glycoprotein, lipoprotein, nucleoside, nucleotide, oligonucleotide, nucleic acid, sugar, carbohydrate, oligosaccharide, polysaccharide, fatty acid, lipid, hormone, metabolite, cytokine, chemokine, receptor, neurotransmitter, antigen, allergen, antibody, substrate, metabolite, cofactor, inhibitor, drug, pharmaceutical, nutrient, prion, toxin, poison, explosive, pesticide, chemical warfare agent, biohazardous agent, radioisotope, vitamin, heterocyclic aromatic compound, carcinogen, mutagen, narcotic, amphetamine, barbiturate, hallucinogen, waste product and/or contaminant. In certain embodiments of the invention, one or more analytes may be labeled with one or more Raman labels, as disclosed below. The sample such as an analyte in the embodiments of this invention could be in the form of solid, liquid or gas. The sample could be analyzed by the embodiments of the method and device of this invention when the sample is at room temperature and at lower than or higher than the room temperature.

The term "label" or "tag" is used to refer to any molecule, compound or composition that can be used to identify a sample such as an analyte to which the label is attached. In various embodiments of the invention, such attachment may be either covalent or non-covalent. In non-limiting examples, labels may be fluorescent, phosphorescent, luminescent, electroluminescent, chemiluminescent or any bulky group or may exhibit Raman or other spectroscopic characteristics.

A "Raman label" or "Raman tag" may be any organic or inorganic molecule, atom, complex or structure capable of producing a detectable Raman signal, including but not limited to synthetic molecules, dyes, naturally occurring pigments such as phycoerythrin, organic nanostructures such as $C_{60}$, buckyballs and carbon nanotubes, metal nanostructures such as gold or silver nanoparticles or nanoprisms and nano-scale semiconductors such as quantum dots. Numerous examples of Raman labels are disclosed below. A person of ordinary skill in the art could realize that such examples are not limiting, and that "Raman label" encompasses any organic or inorganic molecule, compound or structure known in the art that can be detected by Raman spectroscopy.

"Raman spectroscopy" is one analytical technique that provides rich optical-spectral information, and surface-enhanced Raman spectroscopy (SERS) has proven to be one of the most sensitive methods for performing quantitative and qualitative analyses. A Raman spectrum, similar to an infrared spectrum, consists of a wavelength distribution of bands corresponding to molecular vibrations specific to the sample being analyzed (the analyte). In the practice of Raman spectroscopy, the beam from a light source, generally a laser, is focused upon the sample to thereby generate inelastically scattered radiation, which is optically collected and directed into a wavelength-dispersive spectrometer in which a detector converts the energy of impinging photons to electrical signal intensity.

Among many analytical techniques that can be used for chemical structure analysis, Raman spectroscopy is attractive for its capability to provide rich structure information from a small optically-focused area or detection cavity. Compared to a fluorescent spectrum that normally has a single peak with half peak width of tens of nanometers to hundreds of nanometers, a Raman spectrum has multiple bonding-structure-related peaks with half peak width of as small as a few nanometers. Furthermore, surface enhanced Raman scattering (SERS) techniques make it possible to obtain a $10^6$ to $10^{14}$ fold Raman signal enhancement. Such huge enhancement factors are attributed primarily to enhanced electromagnetic fields on curved surfaces of coinage metals. Although the electromagnetic enhancement (EME) has been shown to be related to the roughness of metal surfaces or particle size when individual metal colloids are used, SERS is most effectively detected from aggregated colloids. It is known that chemical enhancement can also be obtained by placing molecules in a close proximity to the surface in certain orientations.

Analyses for numerous chemicals and biochemicals by SERS have been demonstrated using: (1) activated electrodes in electrolytic cells; (2) activated silver and gold colloid reagents; and (3) activated silver and gold substrates. None of the foregoing techniques is capable of providing quantitative measurements, however. Consequently SERS has not gained widespread use. In addition, many biomolecules such as proteins and nucleic acids do not have unique Raman signatures because these types of molecules are generally composed of a limited number of common monomers.

SERS effect is attributed mainly to electromagnetic field enhancement and chemical enhancement. It has been reported that silver particle sizes within the range of 50-100 nm are most effective for SERS. Theoretical and experimental studies also reveal that metal particle junctions are the sites for efficient SERS.

As used herein, "Michael reaction", "Michael addition" or "conjugate addition of an enolate to conjugated carbonyl compound" may be defined generally as an organic reaction, where a conjugated unsaturated carbonyl compound is alkylated to produce a larger molecule with a larger carbon skeleton. It is an alkylation of an electrophilic alkene, belonging a larger class of reactions of conjugate additions. As originally defined, the reaction is the addition of an enolate of a ketone or aldehyde to an α,β-unsaturated carbonyl compound at the β carbon. A newer definition accepted in the art is the 1,4-addition of a doubly stabilized carbon nucleophile to an α,β-unsaturated carbonyl compound.

An "MES" buffer, as used herein, refers generally to commercially available products comprising a 2-morpholineethanesulphonic acid. Unless otherwise specified, the MES buffer solutions used are 0.1 molar (M) solutions with a pH of 6.0.

"IMAC" refers to Immobilized Metal Affinity Chromatography, which is generally a method for protein purification using chromatography. Other methods of protein/peptide enrichment which may be referred to include titanium oxide and antibody chromatography. Each of these methods differs in the column material employed in the chromatography process. As different column materials may have different affinities toward certain target compounds, they may provide alternative means of peptide/protein enrichment.

The term "hydrazide" may refer to any constituents of a class of organic compounds having the general structure: $R_1R_2$—N—N—$R_3R_4$, wherein at least one of $R_1$-$R_4$ is an acyl group. Unless otherwise specified, in at least one embodiment of the present invention, at least one of $R_1$-$R_4$ is a label or tag. Such tags/labels may be fluorescent, phosphorescent, luminescent, electroluminescent, chemiluminescent or any bulky group or may exhibit Raman or other spectroscopic characteristics.

Also referred to herein may be "High Performance Liquid Chromatography" ("HPLC") which is an analytical technique for the separation of organic and inorganic solutes in a sample. Generally, the process refers to a liquid chromatographic process in which liquid permeates a porous solid stationary phase and elutes the solutes into a flow-through detector. The stationary phase is usually in the form of small-diameter (5-10 mm) uniform particles, packed into a cylindrical column. The typical column is constructed from a rigid material (such as stainless steel or plastic) and is generally 5-30 cm long and the internal diameter is in the range of 1-9 mm.

The term "derivatize" means to alter the chemical composition of a molecule by a chemical reaction which changes some part of the molecule, and preferably leaving most of the molecule unchanged.

A "Raman label" or "Raman tag" may be any organic or inorganic molecule, atom, complex or structure capable of producing a detectable Raman signal, including but not limited to synthetic molecules, dyes, naturally occurring pigments such as phycoerythrin, organic nanostructures such as $C_{60}$, buckyballs and carbon nanotubes, metal nanostructures such as gold or silver nanoparticles or nanoprisms and nano-scale semiconductors such as quantum dots. Numerous examples of Raman labels are disclosed below. A person of ordinary skill in the art could realize that such examples are not limiting, and that "Raman label" encompasses any organic or inorganic molecule, compound or structure known in the art that can be detected by Raman spectroscopy.

The term "fluid" used herein means an aggregate of matter that has the tendency to assume the shape of its container, for example a liquid or gas. Analytes in fluid form can include fluid suspensions and solutions of solid particle analytes.

The term "hydrolytic stability" of a compound refers, generally, to its ability to resist chemical decomposition (hydrolosis) in the presence of water or an aqueous solution. In the present context, this may refer to the differences certain composition exhibit toward decomposition in the same, or similar, conditions. Hydrolysis is a chemical reaction or process in which a molecule is split into two parts by reacting with a molecule of water, which has the chemical formula $H_2O$. One of the parts gets an OH— from the water molecule and the other part gets an H+ from the water. As hydrolysis may be a reversible reaction, condensation and hydrolysis can take place at the same time, with the position of equilibrium determining the amount of each product. The word hydrolysis is often applied to solutions of salts and the reactions by which they are converted to new ionic species or to precipitates (oxides, hydroxides, or salts).

The term "enrichment" is a process of increasing the concentration of specific target molecules. The relative amount of specific target molecules within a complex sample are increased. For example, tyrosine phosphorylation plays a key role in cell signaling for higher eukaryotes. It is estimated that only 0.05% of total protein phosphorylation occurs at tyrosine, so enrichment for tyrosine phosphorylation components could be used for sample preparation prior to analysis.

The term "capture" is a process to save a particular state, for example the phosphorylation state of proteins. The phosphoprotein-binding properties of the resin allow efficient capture of both native and denatured proteins. Therefore, cell or tissue samples can be denatured in lysis buffers and stored in the freezer prior to the phosphoprotein enrichment procedure.

The term "phosphocompound" refers to any molecules containing one or multiple phosphate groups.

The term "phosphopeptide" refers to a phosphorylated peptide on serine, threonine, tyrosine, arginine, lysine or histidine.

The term "imidazole resin" refers to a solid phase containing imidazole functional groups.

This invention relies upon the difference in hydrolytic stability between a carboxylic imidazolide and a phosphate imidazolide, and the low pKa values of hydrazide, to selectively enrich and derivatize phosphocompounds in one step. By performing the enrichment process in a single step, functional groups such as amine and carboxylic acid do not need to be protected and are not affected. Only the target phosphate groups are captured and derivatized.

Methods presently known in the art only permit enrichment and labeling of phosphoproteins in separate steps. Immobilized metal affinity chromatography (IMAC) and phosphor specific antibody resin chromatography are commonly used tools to enrich phosphoproteins. Thereafter, beta-elimination followed by Michael addition is commonly used to derivatize the phosphate group for improved detection sensitivity in mass spectrometry. The purpose of applying beta-elimination is to generate a structure which can nucleophiles for Michael addition reactions. Other mechanisms to introduce such structures can also be used. For examples, linking an alpha, beta-unsaturayed double bond to the phosphate through phosphoramidate chemistry.

According to an embodiment of the present method, enriching and derivatizing phosphocompounds in a single step can be achieved without protecting the carboxylic or amine groups of the biomolecules.

For example, FIG. 1 shows that in the presence of an MES buffer of pH 6.0, an imidazole resin may combine with a phosphopeptide in the presence of a condensing agent, such as 1-ethyl-3-(3-dimethylaminopropyl) carbodiimide. In that reaction, a hydrogen atom is donated by the phosphate group attached to the peptide and one of the nitrogen atoms in the imidazole ring. These sites are then available for bonding the imidazole resin to the phosphate group.

Once bound together, a solution containing the tagging or labeling compound may be added in the form of a constituent of a hydrazide. Under slightly acidic conditions, the hydrazide has relatively low pKa value. Further, the carboxylic imidazole will exhibit a greater degree of hydrolytic instability than the phosphate imidazole, thereby resulting in the replacement of the imidazole resin in the phophopeptide with the tag/label containing hydrazide. Since these conditions are not conducive to reaction with the amine or carboxylic acid functional groups, they do not need to be protected as they are with prior art methods. This permits the derivatization and enrichment to occur in a single step of the process when the label-containing hydrazide is added.

Stated generally, an embodiment of the present invention permits the single stage enrichment and derivatization of an organic phosphocompound. Through Michael addition, a derivatization compound replaces an intermediate compound bonded to a proton donor site on the phosphate group, by virtue of having a relatively low pKa value and because the intermediate compound exhibits a greater degree of hydrolytic instability than the organic phosphocompound under a given set of conditions.

The embodiment shown in FIG. 1 of a one step enrichment and derivatization method for a compound containing a phosphate group graphically depicts the following example in which the derivatization compound is a hydrazide having a label or tag attached thereto. The intermediate compound is an imidazole resin; and the organic phospho-compound is a phosphopeptide. Those skilled in the art will recognize that many alternatives exist for the intermediate compound and phosphopeptide, which may, for example, be replaced with any phosphoproteins. Further, the embodiments of the present invention have application in many areas of scientific study where labeling of phosphocompounds is desirable for analysis and detection purposes.

Example 1

Single-Step Derivation and Enrichment of an Imidazole

The method may be carried out by washing and equilibrating an imidazole resin with an MES buffer (0.1 M, pH 6.0). A sample containing a target phosphocompounds may then be dissolved in the MES buffer. The moisturized imidazole resin is added to the solution followed by addition of EDAC (1-ethyl-3-(3-dimethylaminopropyl) carbodiimide), which is used as a condensing agent.

The resulting slurry may then be incubated at room temperature for 3 hours and subsequently filtered and washed with MES buffer. The solution may then be added to a hydrazide in MES buffer. The hydrazide includes at least one group that comprises the label or tag. Such a label or tag may be fluorescent, phosphorescent, luminescent, electroluminescent, chemiluminescent, a COIN particle, or any bulky group or may exhibit Raman or other spectroscopic characteristics.

The slurry can then be incubated at room temperature for 6 to 12 hours. The resin is then filtered-off and the enriched and derivatized phosphocompound can be collected. The filtrate is desalted or purified using high performance liquid chromatography to obtain a purified sample of derivatized target molecules, which in the case of FIG. 1 is a phosphopeptide having a label or tag attached.

FIG. 1 shows the one-pot process of phosphopeptide enrichment and derivatization. The process started by washing and equilibrating an imidazole resin with an MES buffer (0.1 M, pH 6.0). A sample containing a target phosphocompounds may then be dissolved in the MES buffer first and then added to the imidazole resin, followed by addition of EDAC (1-ethyl-3-(3-dimethylaminopropyl) carbodiimide), which is used as a condensing agent. The resulting slurry may then be incubated at room temperature for 3 hours and subsequently filtered and washed with MES buffer. The solution may then be added to a hydrazide in MES buffer. The hydrazide includes at least one group that comprises the label or tag. Such a label or tag may be fluorescent, phosphorescent, luminescent, electroluminescent, chemiluminescent, a COIN particle, or any bulky group or may exhibit Raman or other spectroscopic characteristics. The slurry can then be incubated at room temperature for 6 to 12 hours. The resin is then filtered-off and the enriched and derivatized phosphocompound can be collected. The filtrate is desalted or purified using high performance liquid chromatography to obtain a purified sample of derivatized target molecules.

Figure 2:
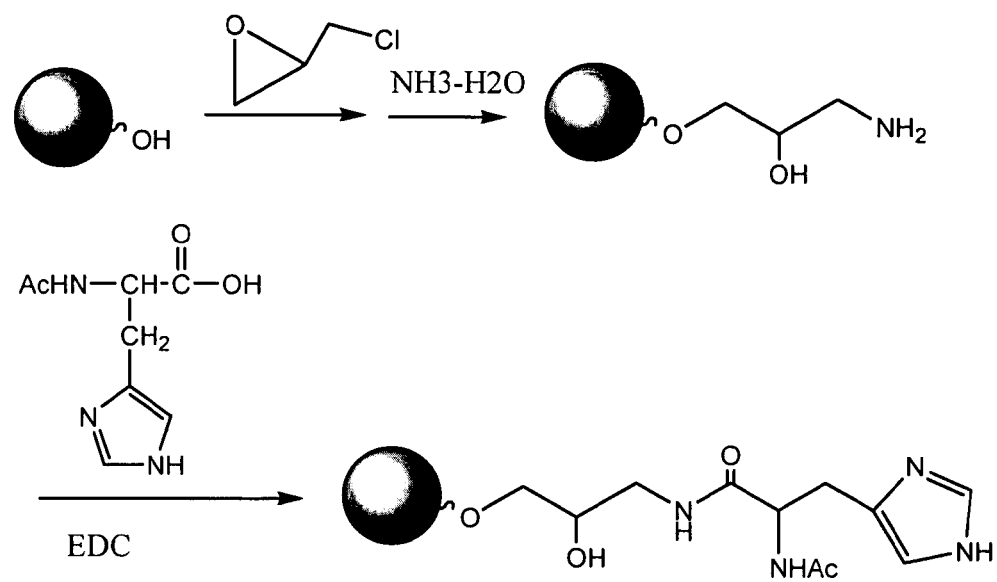
FIG. 2 illustrates an embodiment of the reaction of the present invention and intermediaries formed.

FIG. 2 further illustrates a mechanism for the synthesis of imidazole resin or polymer, wherein the resin is shown generically as a shaded sphere. FIG. 2 shows attachment of imidazole on resin or polymer or other carrier molecules: The resin was first activated by epichlorohydrin under basic condition to introduce an epoxy functional group. The epoxy was then converted to an amino group, which was then coupled with acetylated histadine. The choice of polymers or other carrier molecules can be natural polymers, synthetic polymers, dentrimer, or proteins. Examples are, but not limited to, dextran, bovine serum albumin, sepharose, polyacrylamide derivatives.

Figure 3A:
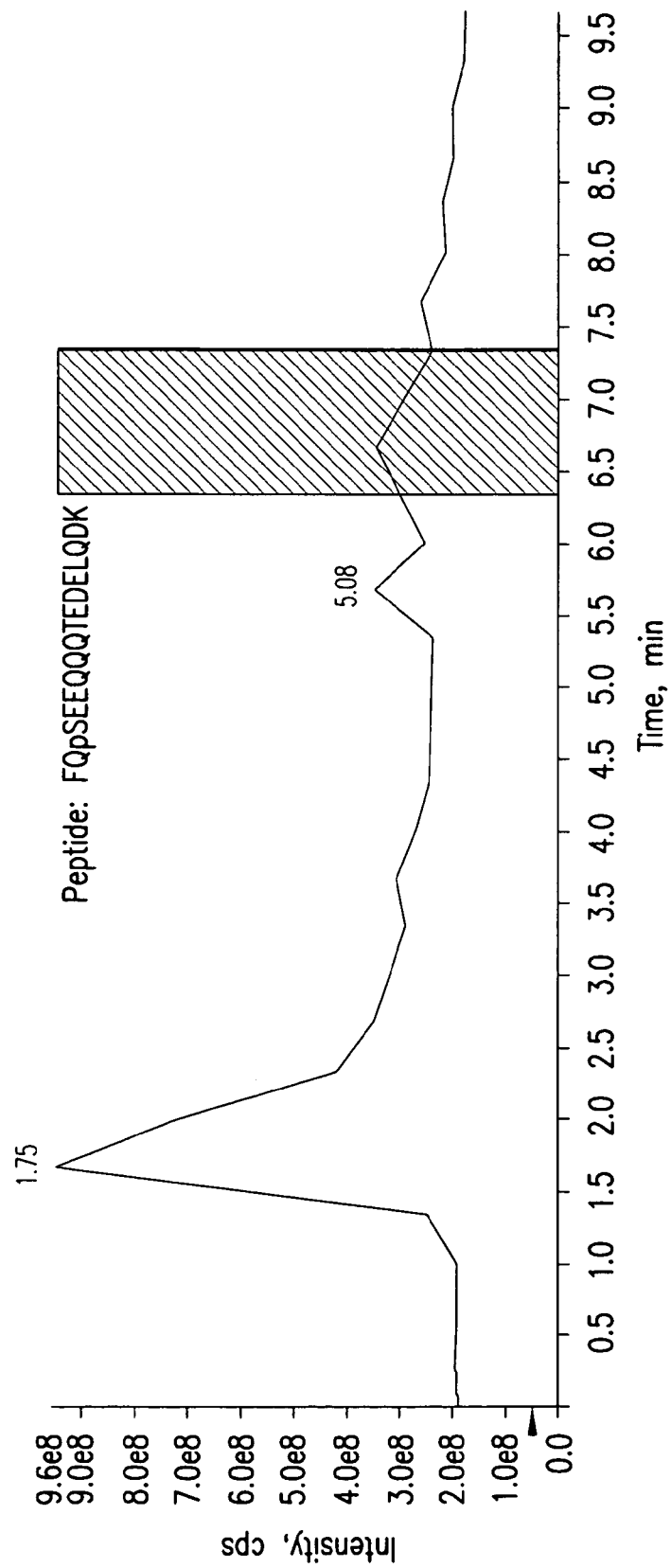
FIGS. 3A and 3B show the spectroscopic analysis of the product of an embodiment of the present invention using peptide SEQ ID No:1.
Figure 3B:
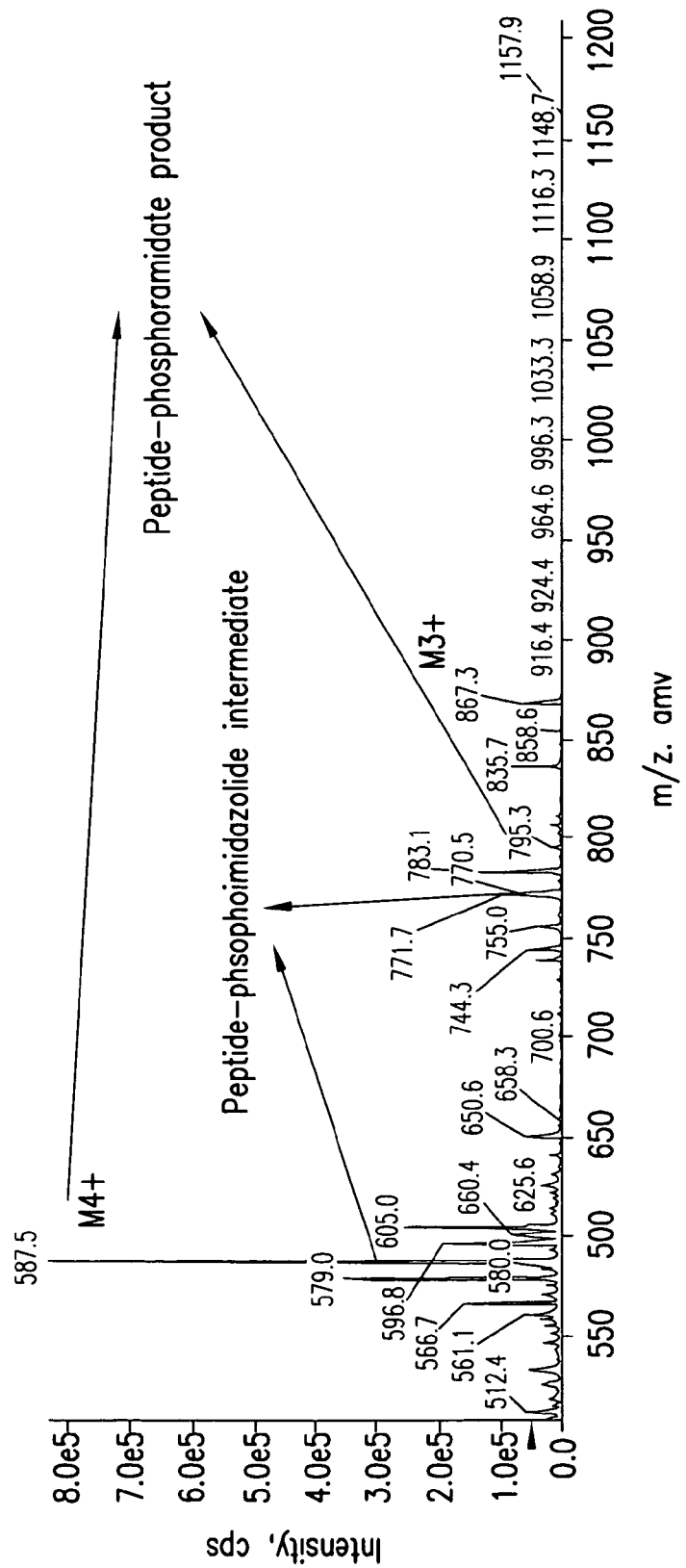

FIG. 3 illustrates a spectroscopic analysis in which the phosphoramidate chemistry is in solution with an exemplary peptide FOXEEQQQTEDELQDK (SEQ ID NO: 1, x=phosphoserine) characterized by Liquid Chromatography and Mass Spectrometry. FIGS. 3A and 3B show LC/MS analysis of a derivatized phosphopeptide intermediate. An Agilent model 1100 (binary) high-performance liquid chromatograph coupled with a hybrid triple quadrupole/linear ion trap mass spectrometer, model 4000 Q TRAP LC/MS/MS system (Applied Biosystems MDS SCIEX) was used in all analyses. The analytical column was Agilent Zorbax SB-C18, 5 μM, 150 mm×0.5 mm. The injection volume was 5 μL. The mobile phase consisted of (A) 0.1% formic acid in water (v/v); (B) 0.1% formic acid in acetonitrile (v/v) at a flow rate of 30 μL/min under a linear gradient of 0% B to 80% B over 30 min. MS data were acquired in the positive ion electrospray ionization (ESI) mode, using the following TurbolonSpray source conditions: temperature=500° C., curtain gas=40 (arbitrary units), GS1=70, GS2=60, CAD gas pressure high, ion spray voltage=5500V.

This application may disclose numerical range limitations that support any range within the disclosed numerical ranges even though a precise range limitation is not stated verbatim in the specification because the embodiments of the invention could be practiced throughout the disclosed numerical ranges. Finally, the entire disclosure of the patents and publications referred in this application, if any, are hereby incorporated herein in entirety by reference.

The invention claimed is:

1. A method comprising:
    obtaining a phosphate group having a proton donor site, attaching a derivatization compound to the proton donor site by Michael addition, wherein the derivatization compound has the formula $R_1R_2$—N—N—$R_3R_4$, wherein $R_1$-$R_4$ are reactive groups, wherein at least one of $R_1$-$R_4$ is an acyl group, wherein at least one of $R_1$-$R_4$ is a label, and wherein the phosphate group is connected to an imidazole resin or a carboxylic imidazole at the proton donor site.

2. The method of claim 1, wherein the phosphate group is part of a phosphopeptide, phosphoprotein, a phosphonucleotide or a phosphooligonucleotide.

3. The method of claim 1, wherein the label is fluorescent phosphorescent, luminescent, electroluminescent, or chemiluminescent.

4. The method of claim 1, wherein the label exhibits Raman or other spectroscopic characteristics.

5. The method of method of claim 1, wherein the label is a composite-organic-inorganic nanoparticle (COIN).

6. The method of claim 1, wherein the derivatization compound is a hydrazide.

7. The method of claim 1, wherein obtaining the phosphate group connected to the imidazole resin comprises a reaction in the presence of a condensing agent.

8. The method of claim 7, wherein the condensing agent is 1-ethyl-3-(3-dimethylaminopropyl) carbodiimide.

9. The method of claim 2, wherein the phosphopeptide is SEQ ID No: 1 (FQpSEEQQQTEDELQDK).

10. The method of claim 1, wherein the phosphate group is in a slurry.

11. The method of claim 1, wherein the label is a Raman label.

* * * * *